(12) United States Patent
Fischer et al.

(10) Patent No.: US 8,017,790 B2
(45) Date of Patent: Sep. 13, 2011

(54) METHOD FOR PRODUCING PYRROLIDONES FROM SUCCINATES FROM FERMENTATION BROTHS

(75) Inventors: Wolfgang Fischer, Lingenfeld (DE); Daniela Klein, Mannheim (DE); Andreas Künkel, Neustadt (DE); Rolf Pinkos, Bad Dürkheim (DE); Edzard Scholten, Mannheim (DE)

(73) Assignee: BASF SE, Ludwigshafen (DE)

( * ) Notice: Subject to any disclaimer, the term of this patent is extended or adjusted under 35 U.S.C. 154(b) by 619 days.

(21) Appl. No.: 11/722,263

(22) PCT Filed: Dec. 17, 2005

(86) PCT No.: PCT/EP2005/013630
§ 371 (c)(1),
(2), (4) Date: Jun. 20, 2007

(87) PCT Pub. No.: WO2006/066839
PCT Pub. Date: Jun. 29, 2006

(65) Prior Publication Data
US 2010/0044626 A1    Feb. 25, 2010

(30) Foreign Application Priority Data
Dec. 21, 2004   (DE) .................. 10 2004 062 717

(51) Int. Cl.
*C07D 207/12*   (2006.01)
(52) U.S. Cl. ........................................ 548/545
(58) Field of Classification Search .......... None
See application file for complete search history.

(56) References Cited

U.S. PATENT DOCUMENTS

| | | | |
|---|---|---|---|
| 3,910,951 A | 10/1975 | Fuerst et al. | |
| 4,841,069 A | 6/1989 | Olsen | |
| 6,603,021 B2 * | 8/2003 | Werpy et al. | 548/552 |
| 2004/0176589 A1 * | 9/2004 | Werpy et al. | 540/201 |

FOREIGN PATENT DOCUMENTS

| | | |
|---|---|---|
| DE | 2313386 | 9/1974 |
| EP | 410728 | 1/1991 |
| WO | WO-02/102772 A1 | 12/2002 |

OTHER PUBLICATIONS

"Annalen der Chemie und Pharmacie", Justus Liebigs Ann. Chem., 1844, vol. 49, pp. 154-212.
Clarke, "Organic Syntheses", 1943, vol. II, pp. 562-563.

* cited by examiner

*Primary Examiner* — Yong Chu
*Assistant Examiner* — Michael Barker
(74) *Attorney, Agent, or Firm* — Connolly Bove Lodge & Hutz LLP

(57) ABSTRACT

The present invention relates to a process for preparing a compound II or a composition comprising the compound II

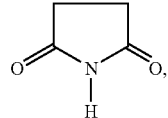

(compound II)

to a composition comprising succinimide and to a composition prepared by the process according to the invention.

13 Claims, No Drawings

METHOD FOR PRODUCING PYRROLIDONES FROM SUCCINATES FROM FERMENTATION BROTHS

RELATED APPLICATIONS

This application is a national stage application (under 35 U.S.C. §371) of PCT/EP2005/013630 filed Dec. 17, 2005, which claims benefit of German application 10 2004 062 717.7 filed Dec. 21, 2004.

Succinic acid and its derivatives are important precursors for a number of products of economic interest and find use, for example, in the preparation of alkyd and polyester resins, solvents or a number of specialty chemicals; see Zeikus, Appl. Microbiol. Biotechnol, 1999, 545-552. Pyrrolidones, which are occasionally also known as pyrrolidinones, are prepared essentially by petrochemical means from the reaction of gamma-butyrolactone with ammonia (2-pyrrolidone) or with methylamine (N-methylpyrrolidone), or in general terms with alkylamine (N-alkylpyrrolidone). N-Alkylpyrrolidones, for example NMP, find use, for example, in the electronics industry as solvents, 2-pyrrolidone is an important solvent and extractant and serves predominantly as an intermediate for the preparation of N-vinylpyrrolidone, which is in turn an important monomer.

To date, only a relatively small market has existed for succinic acid, which is generally prepared by petrochemical means from maleic anhydride or butanediol, but there has been a great deal of research in the field of fermentative preparation in the last few years, such that industrial fermentative preparation of succinic acid as an intermediate for C4 chemicals in the near future appears to be possible; Miller, Varadarajan in Biotechnol. Prog. 1999, 15, 845-854. Numerous purification methods for the isolation of succinic acid or succinic salts from fermentation broths have been described. Succinic acid is obtained from fermentation broths, for example, with the aid of filtration, crystallization, extraction, electrodialysis, chromatography: U.S. Pat. Nos. 5,034,105, 4,670,155, 5,814,498, 5,168,055, 5,958,744, 5,780,276, 5,143,834, 5,143,833, 5,412,1.26, 5,104,492, 4,670,155.

The purified succinic acid and its salts, or esters thereof, are generally converted to N-alkylsuccinimide (U.S. Pat. Nos. 4,841,069, 4,814,464) or directly to 2-pyrrolidone (U.S. Pat. Nos. 3,080,377, 3,198,808, 3,681,387, 4,263,175) or NMP (U.S. Pat. Nos. 3,448,118, 5,157,127, 5,434,273, WO02/102772).

Processes in which pyrrolidones are prepared from succinimide have also been described. Succinimide itself can be prepared, according to JP 04282361, from succinic acid and ammonia in the presence of phosphite. SU 1317890 describes the preparation of succinimide from succinic acid and urea, while, according to Zh. Obshch. Khim.; 20, 1950, 1145, 1149, 1191, 1195, succinimide can be prepared together with succinic monoamide from succinic acid in the presence of pyridine and sulfamide. Further processes for preparing succinimide are described, for example, in Yakugaku Zasshi; 62; 1942; 532, 169, where succinimide is prepared from succinic acid with formamide, Recl. Trav. Chim. Pays-Bas; 75; 1956; 164, 167; J. Indian Chem. Soc.; 10; 1933; 111, 114, which describe the preparation of succinimide from succinic acid and urea, and in the publications J. Chem. Soc.; 1931; 443 (Preparation of succinimide from succinic acid and ammonium carbonate), Chem. Ber.; 23; 1890; 3285 (Preparation of succinimide from succinic monoamide) and Justus Liebigs Ann. Chem.; 49; 1844; 197 (Preparation of succinimide from succinic diamide).

Clarke, Org. Synth. 1943, II, 562 describes the conversion of chemically pure diammonium succinate to succinimide by a reactive distillation with subsequent distillation. In a first stage, the aqueous diammonium succinate solution is concentrated until a melt is present, and then, in a second stage, the succinimide is distilled off overhead. For example, a crystallization of the succinimide in 95% ethanol is performed in order to achieve a maximum purity.

DT 2313386 describes the chemical conversion of succinic acid in the presence of ammonia and triammonium phosphate to succinimide.

WO 02/102772 describes a process for preparing N-methylpyrrolidones, in which diammonium succinate is hydrogenated to form a mixture of 2-pyrrolidone and N-methylpyrrolidone.

In the preparation of conversion products, for example pyrrolidones, from succinic acid and its derivatives prepared by fermentation, the successful performance of the reaction steps often requires the intermediates to be purified. For the workup of succinic acid or its derivatives (for example salts or esters) from fermentation broths, apparatus- and time-consuming process steps, for example crystallization, precipitation, electrodialysis, extraction or chromatography, are often proposed in order to achieve sufficient removal of the, for example, catalyst-damaging ingredients (possibly nutrient constituents, metabolism by-products, cell constituents). Since a combination of these process steps is often described as necessary, especially for succinic acid and its salts, the resulting costs have to date been a hindrance for an industrial process for converting fermentative succinic acid to comparatively low-cost products, for example pyrrolidones. In addition, in some of these workup processes, recycling of the base used in the fermentation is not possible, which causes additional costs with regard to feedstocks and disposal.

It is thus an object of the present invention to provide a process which allows inexpensive preparation of succinimide and possible conversion products, especially substituted and unsubstituted pyrrolidones, from contaminated succinate-containing solutions, i.e. from solutions which comprise many secondary components, for example fermentation broths.

The problem underlying this invention is solved by the provision of the process according to the invention described herein and the embodiments characterized in the claims.

Consequently, the present invention relates to a process for preparing the succinimide intermediate or a composition which comprises succinimide, and in which pyrrolidones can be prepared in further inventive steps. The process according to the invention is characterized by the embodiments described herein.

In one embodiment, the present invention consequently relates to a process for preparing the compound II or a composition comprising the compound II,

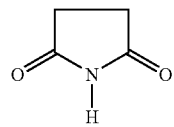

(compound II)

the process comprising at least the following steps:
(a) providing a fermentation broth, which, in a further embodiment, has been pretreated, for example by biomass removal, sterilization and/or concentration, comprising the compound I

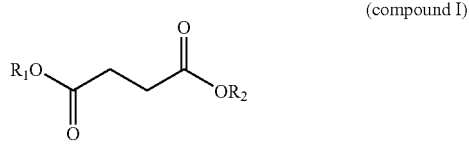

(compound I)

where $R_1$ may be $NH_4^+$, $H^+$ or another cation and $R_2$ may be $NH_4^+$, $H^+$ or another cation, and where at least $R_1$ or $R_2$ is $NH_4^+$;

(b) converting the compound I in the fermentation broth to the compound II;

(c) simultaneously, intermittently or subsequently distillatively removing ammonia and/or water;

(d) subsequently distilling the bottoms of the distillation of step (c) under reduced pressure to form a distillate comprising the compound It;

(e) isolating the compound II or converting the distillate from step (d).

In step (c), water which forms in the reaction or else is present in the broth is distilled off partly or completely. Ammonia is formed only when $R_1$ and $R_2$ are ammonium. In addition, it is also possible for other volatile substances, in particular substances which are lighter than succinimide to also be distilled off, for example ethanol which can form as a by-product in the fermentation. The cations are essentially cations which are typically present in fermentation broths or preparations thereof. In a further embodiment, the cation is a monovalent cation, for example one of the following cations: Na+ and/or K+. In a further embodiment, the cation is a divalent cation, for example $Mg^{2+}$ and/or $Ca^{2+}$. In a further embodiment, a mixture of different cations is present, for example Na+ and/or K+. In a further embodiment, the cation is a divalent cation, for example $Mg^{2+}$ and/or $Ca^{2+}$ and/or other cations, for example of trace elements.

Surprisingly, in the process according to the invention, the compound II is obtained in a composition which enables direct further conversion, for example in a hydrogenation, of the compound II and any other constituents of the composition, without one or more further purification step(s) being required. Especially taking account of the "fermentation broth" starting material, this is surprising. Advantageously, the process according to the invention also converts derivatives, for example monoamide of succinic acid, which are present in the resulting mixture, to pyrrolidones, so that there is surprisingly a uniform conversion of the succinimide in spite of the many secondary components that the fermentation broth comprises before the reaction in the process according to the invention.

Workups of metabolism products prepared in fermentation methods often require special purification steps, since unconverted or incompletely converted constituents of the medium, degradation products of constituents of the medium, by-products formed and their degradation products, constituents released by lyzed cells and their degradation products, for example salts, polysaccharides, proteins, peptides and amino acids, amines, amides, organic acids, alcohols, aldehydes and/or ketones, the particular degradation products and/or other organic and inorganic compounds can inhibit further chemical reaction or not lead to a purification effect which is allowed by a subsequent reaction without intermediate purification. Advantageously, compound I is thermally stable. In the present process according to the invention, time-consuming and expensive purification steps of the compound I, for example chromatography, electrodialysis or crystallization, are dispensed with. It is additionally advantageous that any ammonia formed is recovered in the form of aqueous ammonium hydroxide solution and can be reused in the fermentation. The process according to the invention allows the risk of catalyst poisoning to be lowered by secondary constituents of the fermentation broth and the distillative purification of the end products to be eased, because most by-products from the fermentation are removed in the distillation of the compound II or of the composition comprising the compound II.

Consequently, in a preferred embodiment, the compound II and/or the abovementioned derivatives are reacted without further isolation or intermediate purification, for example as described below, especially in a hydrogenation.

Consequently, in a further embodiment in the present process, the ammonia formed is recovered and preferably used again in the fermentation, for example as an aqueous ammonium hydroxide solution.

The conversion of compound I to compound II forms the intermediates compound Ha and compound IIb:

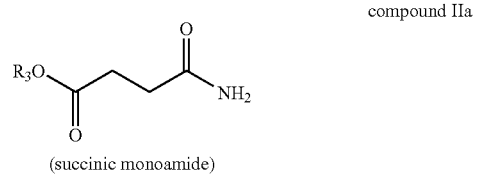

(succinic monoamide)

where $R_3$ may be $H^+$ or another cation, preferably a cation which is a medium constituent, for example a cation as listed above or $NH_{4+}$;

and/or

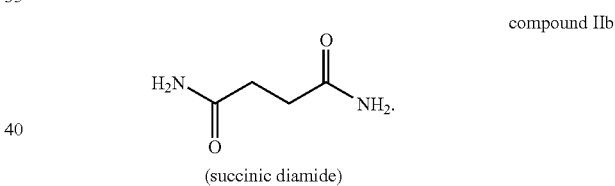

(succinic diamide)

Depending on the selection of the parameters, the particular proportion of compound II and/or IIa and/or IIb can be varied and determined in the process according to the invention. In one embodiment, the residence times in the upper region of the temperature interval are longer, and the water formed and any ammonia formed are distilled off essentially completely, for example to an extent of at least 50%, preferably to an extent of 60%, 70%, 80%, 90%, 95%, 97%, 99% or more. Water is preferably distilled off completely. Consequently, the invention relates, in one embodiment, to a process according to the invention in which a composition comprising succinimide and/or succinic monoamide and/or succinic diamide is prepared.

In one embodiment, in the process according to the invention, the parameters are selected so as to obtain a melt comprising compound II. Consequently, in one embodiment, the temperature is above the melting point of the melt. The melting point of succinimide is between about 120° C. to 130° C.; the melting point of a succinimide-containing melt is, depending on the degree of contamination, below the melting point of succinimide. In one embodiment, the melt is kept at a temperature greater than 120° C., for example greater than 126° C.

In one embodiment, the distillation of water and/or ammonia and any other relatively volatile substances takes place essentially parallel to the reaction.

According to the invention, in one embodiment, the distillation of the succinimide is effected after the distillation of water and ammonia.

In one embodiment, the invention relates to a composition which comprises succinimide and also at least succinic monoamide or at least succinic monoamide and succinic diamide. Depending on the selection of the process parameters, the process according to the invention forms a mixture which comprises succinimide, succinic acid, succinic monoamide and/or succinic diamide in different proportions. The remaining secondary fermentation constituents are preferably essentially removed. Advantageously, in the process according to the invention, irrespective of the proportions in which succinimide and succinic monoamide and/or succinic diamide are present in the distillation bottoms after step (c), a product is obtained which, surprisingly, can provide succinimide, succinic monoamide and/or succinic diamide in a form which allows a reaction without further workup.

In one embodiment, consequently, the reaction of the distillate from step (d) or the further processing of the distillate from step (d) is effected without further workup. In particular, in one embodiment, the distillate from step (d) can be converted to pyrrolidones without further workup, or be dissociated to succinic acid or its salts or succinic acid derivatives.

Surprisingly, the product of the distillation from step (d), comprising compound II, IIa and/or IIb, can be converted further directly by reduction to compound IIa. In particular, surprisingly, an inventive reduction of a composition comprising compound II and IIa and/or IIb converts not only compound II but also compounds IIa and IIb, possibly via the intermediate compound II, to the compound IIa. Consequently, in one embodiment, through the inventive further process steps described herein, the distillate from step (d) is converted to 2-pyrrolidone with high yields.

Optionally, the compound II, for example succinimide or a composition comprising succinimide, succinic acid, succinic monoamide and/or succinic diamide can be worked up further from the melt, for example purified further.

In one embodiment, the present invention consequently relates to a process for preparing the compound IIIa or a composition comprising the compound IIIa

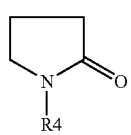

(compound III)

where R₄ is H (compound IIIa), or
and where the process comprises the steps of the process according to claim 1 or 2, followed by:
(f) reducing the compound II to the compound III.

Surprisingly, it is thus possible with the present process to convert a compound I which is present in a fermentation broth to the compound IIIa and/or IIIb by conversion to the compound II and simple distillation or the like, or to the compounds IIa and/or IIb, with avoidance of a costly purification of compound I by means of electrodialysis, crystallization, extraction, etc.

In particular, it is thus advantageously possible with the process according to the invention to prepare substituted or unsubstituted pyrrolidones as desired, especially 2-pyrrolidone. Consequently, in one embodiment, the reduction, as described below, is a hydrogenation.

It is particularly advantageous that the process according to the invention provides, inexpensively and without time-consuming purification steps, a composition comprising essentially 2-pyrrolidone. In one embodiment, the 2-pyrrolidone prepared in accordance with the invention does not comprise any NMP.

In one embodiment, the present invention consequently relates to a process for preparing a compound IIIb or a composition comprising the compound IIIb, in particular a composition comprising the compound IIIa and IIIb

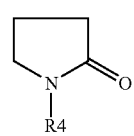

(compound III)

where R₄ for compound IIIa is H; and
where R₄ for compound IIIb is branched or unbranched alkyl having from 1 to 20 carbon atoms with from 0 to 1 OH or NH₂ radicals;
and where the process comprises the steps of the process according to claim 3, followed by:
(g) completely or partially alkylating the compound IIIa to give the compound IIIb during or after step (f).

In order to prepare substituted pyrrolidones, it is possible to add suitable alkylating agents, for example the alkylating agents mentioned below, to a hydrogenation. For the preparation of an N-alkylpyrrolidone, particular preference is given to using a straight- or branched-chain C1 to C20-alcohol or -alkylamine, preferably a straight- or branched-chain C1 to C4-alcohol, for example methanol, ethanol, propanol or butanol, or a corresponding amine, for example methylamine, ethylamine, butylamine or propylamine. In one embodiment, alkylation is consequently effected in the presence of methanol or ethanol.

In one embodiment, consequently, the 2-pyrrolidone prepared in the process according to the invention is converted to substituted pyrrolidones, for example hydroxyethylpyrrolidone or N-methylpyrrolidone (NMP), or mixtures thereof. Advantageously, the selection of the process parameters allows the 2-pyrrolidone to be converted to a defined mixture of 2-pyrrolidone and substituted pyrrolidones, especially NMP, or virtually completely to substituted pyrrolidones. The selection of the parameters allows the degree of reaction and hence the distribution of the products in the product mixture to be determined. In one embodiment, compound II is converted in the presence of the alkylating agent, for example of an amine such as, inter alia, alkylamine or hydroxyalkylamine or alkyldiamine. The higher the molar ratio of the alkylating agent, for example of alkylamine or hydroxyalkylamine or alkyldiamine, to compound II, the more compound IIIb forms in a mixture with IIIa.

In one embodiment of the process according to the invention, the fermentation broth is prepared by anaerobic or aerobic fermentation or a combination of aerobic and anaerobic fermentation, preferably by the fermentation of carbon sources, for example oils or alcohols, especially glycerol, ethanol, methanol, L-sorbose or D-sorbitol, or sugars, for example C6 or C5 sugars, especially glucose, sucrose, arabinose, xylose or $CO_2$, or $H_2$, in pure form or, for example, as molasses or mixtures of the substances mentioned or their precursors, for example starch, for example together with enzymes, or other possible carbon-containing compositions, for example cellulose, for example in the form of used paper, wood wastes or constituents of starch-containing plants.

For the fermentation, for example, prokaryotic or eukaryotic microorganisms are used, for example bacteria such as *E. coli, Anaerobiopirillum succiniproducens, Actinobacillus succinogenes, Mannheimia succiniproducens* or other bacteria or fungi which produce succinic acid.

In one embodiment, in the fermentation, a microorganism, for example *E. coli*, after an aerobic growth phase to develop biomass, is transferred to anaerobic conditions. The synthesis of succinate takes place in this anaerobic phase. The two cultivation steps can take place especially in complex medium. In a further embodiment, in the fermentation, the cultivation of the microorganism, especially of *E. coli*, in the anaerobic phase is effected with minimal medium. A further embodiment comprises the repeated recycling of the cells and performance of the anaerobic production phase in complex or minimal medium.

The fermentation can be performed in stirred fermenters, bubble columns and loop reactors. A comprehensive overview of the possible embodiments including stirrer types and geometric configurations can be found in "Chmiel: Bioprozesstechnik: Einführung in die Bioverfahrenstechnik, Band 1" [Chmiel: Bioprocess Technology: Introduction into Bioprocess Technology, volume 1]. In the process configuration, the following variants which are known to those skilled in the art or explained, for example, in "Chmiel, Hammes and Bailey: Biochemical Engineering", such as batch, fed-batch, repeated fed-batch, or else continuous fermentation with and without recycling of the biomass, are typically available. Depending on the production strain, sparging with oxygen, carbon dioxide, hydrogen or nitrogen can/must be effected in order to achieve good yields.

Before the reaction in the fermentation broth in the process according to the invention, the fermentation broth can be pretreated; for example, the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. To obtain the product of value substantially completely, washing of the biomass is often advisable, for example in the form of a diafiltration. The selection of the method is dependent upon the biomass content in the fermentation broth and the properties of the biomass, and also the interaction of the biomass with the product of value.

In one embodiment the fermentation broth can be sterilized or pasteurized.

In a further embodiment, the fermentation broth is concentrated. This concentration or evaporation can be done batchwise or continuously as required. Pressure and temperature range should be selected such that, on the one hand, no product damage occurs, and, on the other hand, minimized use of apparatus and energy is needed.

Especially the skillful selection of the pressure and temperature stages for a multistage evaporation enables saving of energy.

In terms of apparatus, stirred tanks, falling-film evaporators, thin-film evaporators, forced-circulation flash evaporators and other evaporator designs in natural or forced circulation mode can be utilized for this purpose.

Consequently, the term "fermentation broth" is understood to mean an aqueous solution based on a fermentative process, which has not been worked up or has been worked up, for example, as described herein.

Depending on the selection of the process parameters, the process according to the invention forms, in the reaction and distillation according to step (b), a mixture which comprises, inter alia, the succinic acid, succinic monoamide, succinimide and succinic diamide products. The proportion of the different products can be varied, for example, by the selection of the residence time, temperature, or of the water and ammonia content. The remaining secondary fermentation constituents are essentially removed in distillation. Surprisingly, the mixture of succinic acid, succinic monoamide, succinimide and succinic diamide can be converted with high yields to pyrrolidones, especially to 2-pyrrolidone. In one embodiment of the process according to the invention, the reaction parameters of the reaction are selected such that a melt comprising essentially succinimide is formed when the temperature of the distillation effluent is kept above the melting point, preferably at >130° C.

The process for preparing succinimide can be performed continuously or batchwise.

In a continuous process, the reaction and distillation is performed under the following conditions:
  (i) preferably, removing the biomass and/or purifying the fermentation broth;
  (ii) preferably, concentrating the fermentation broth;
  (iii) distillatively removing the by-products, for example $H_2O$ and $NH_3$, and converting the compound I in the fermentation broth at a temperature of for example, from about 100 to about 300° C., more preferably at from about 150 to about 200° C., most preferably at about 170° C., for example at standard pressure, until a melt is present; and
  (iv) preferably, postreaction at, for example, from about 150 to about 300° C., preferably from about 200 to about 300° C., more preferably at about 250° C., for example for essentially less than about 2 h, for example for from about 0.5 h to about 1 h and, for example, at standard pressure; and
  (v) distillatively removing the compound II and, if appropriate, compound IIa and IIb, for example at a temperature of from about 150° C. to 300° C., preferably at more than 170° C. and less than 270° C., more preferably at from about 220° C. to about 250° C., the temperature of course depending greatly, as well as the pressure, on the composition, the secondary components and the degree of removal, and, for example, being effected at standard pressure or reduced pressure, preferably at a pressure of 0.01 to 1000 mbar, preferably 1-100 mbar, for example for purification with removal of secondary components.

In one embodiment, the reaction and distillation is performed batchwise under the following conditions:
  (i) preferably, removing the biomass and/or purifying the fermentation broth;
  (ii) preferably, concentrating the fermentation broth;
  (iii) distillatively removing the by-products, for example $H_2O$ and $NH_3$, and converting the compound I at a temperature of from RT up to about 300° C., preferably at standard pressure; and
  (iv) preferably, postreaction at, for example, from about 150 to about 300° C., preferably from about 200 to about 300° C., more preferably at about 250° C., for, for example, less than about 2 h, more preferably for from about 0.5 h to about 1 h and, for example, at standard pressure; and
  (v) preferably, subsequently overdistilling the reaction mixture at reduced pressure and at approx. 150 to approx. 300° C., preferably 170-250° C., for example for purification with removal of secondary components by distillation, more preferably at a temperature of, for example, from about 185 to about 195° C. and, for example, at standard pressure or at reduced pressure, preferably at a pressure of from about 0.01 to about 1000 mbar, preferably at 1-100 mbar, more preferably at about 25 mbar.

In one embodiment, the process according to the invention comprises all process steps (i) to (iii) mentioned, especially at the pressure mentioned and at the temperature mentioned. Preference is given to performing the process under the conditions preferred in each case.

The reaction in step.(i) can be effected, for example, in stirred tanks or other reactors, in various evaporator types, for example falling-film evaporators, in a distillation column or in combinations thereof.

The reactive dryer utilized may also be a spray dryer or a spray granulator, in which case the product is present in solid form and has to be melted or dissolved again thereafter for purification or further reaction.

The secondary components removed in step (iii) are preferably acetate, lactate, formate and media constituents (for example salts, proteins, sugars, amino acids, yeast extract). The content of succinimide, depending on the starting material, is preferably more than 50%, 60% or 70%, preferably more than 80%, even more preferably more than 85%. For example, in continuous mode, a purity of 85% or more succinimide is achieved with a bottoms diluent, especially DAS admixed with Pluriol P600 and minimal medium, and, when fermentation broth is used, after biomass removal (fermented with minimal medium) and supplemented with synth. DAS, 87% or more succinimide.

In batchwise mode, when DAS supplemented with minimal medium is used, a purity of 70-98% succinimide or more can be achieved.

Alternatively to the conversion to succinimide and its distillation, the purification to remove secondary components from the diammonium succinate can also be achieved by means of a release of the succinic acid and crystallization, by means of membrane processes, especially electrodialysis, by means of chromatography or extraction, or other processes known to those skilled in the art.

In one embodiment a 1-50%, preferably less than 30% bottoms diluent, for example polyalkylene glycols, for example Pluriol (trade name), especially Pluriol P600 (trade name), or silicone oils, for example Baysilone (trade name) or paraffin oils are added to the fermentation broth.

Consequently, in one embodiment, the present invention relates to a composition, for example a melt, comprising compound II and bottoms diluent, for example polyalkylene glycols, for example Pluriol (trade name), especially Pluriol P600 (trade name), or silicone oils, for example Baysilone (trade name) or paraffin oils, for example with Pluriol P600.

Preference is given to using sufficient bottoms diluent that the reaction and distillation are improved by sufficiently lowering the viscosity and retaining the stirability of the reaction mixture.

In one embodiment, the invention relates to a composition obtainable by the process according to the invention.

Specifically in the case of preparation of substituted or unsubstituted pyrrolidones, the preparation of succinimide from DAS in the process according to the invention is advantageous, since, even in the case of incomplete conversion, the mixture of DAS, succinic monoamide and diamide and succinimide can be processed further. Consequently, in one embodiment of the process according to the invention, the reduction of the compound II or of the composition comprising the compound II and optionally the compounds IIa and IIb to the compound III is effected by a hydrogenation, for example a catalytic hydrogenation with hydrogen in the presence of homogeneous or heterogeneous catalysts which may, for example, be arranged in suspended or fixed form, or a hydrogenation with complex hydrides, or a transfer hydrogenation in which, for example, alcohols such as methanol or isopropanol release the hydrogen for the hydrogenation with formation of aldehyde or with a ketone.

In a preferred embodiment the reduction of the compound II is a catalytic hydrogenation and can be performed in the gas phase or the liquid phase.

Useful reactors include all types customary for hydrogenations, for example batchwise, for example stirred, or continuous reactors: the reactors used may, for example, be tubular reactors, tube bundle reactors, shaft reactors or fluidized bed reactors.

The hydrogenation can be effected in one stage or several stages, for example with main reactor and postreactor. In this case, the main reactor, at least in the liquid phase, is preferably operated with external circulation for heat removal, and the postreactor preferably in straight pass, in order to achieve maximum conversion. The reaction pressure used in the liquid or gas phase may be the pressures mentioned below.

In the preparation of pyrrolidone, the hydrogenation can be effected with addition of ammonia, but it is not necessary. When ammonia is added, the formation of gamma-butyrolactone can be suppressed, which eases the workup of the reaction effluents. Based on reactant used, ammonia is used in up to a 10-fold, preferably up to a 5-fold, more preferably up to a 2-fold molar excess.

In the workup, products which occur and are yet to be completely converted can generally be recycled in order to increase the yield. Such products are, for example, imides or bisamides.

The hydrogenation catalysts used in the process according to the invention may generally be heterogeneous, but also homogeneous, catalysts suitable for hydrogenating carbonyl groups. They may be used either in fixed bed form or else in mobile form, for example in a fluidized bed reactor. Examples thereof are described, for example, in Houben-Weyl, Methoden der Organischen Chemie [Methods of Organic Chemistry], Volume IV/1c, p. 16 to 26. Among these hydrogenation catalysts, preference is given to those which comprise one or more elements of group 11, 6, 7, 8, 9, 10, 13, 14 and 15 of the Periodic Table of the Elements, especially copper, rhenium, manganese, cobalt, ruthenium, rhodium, nickel, palladium, iron, platinum, indium, tin and antimony. Particular preference is given to catalysts which comprise copper, cobalt, ruthenium or rhenium.

The catalysts used in the process according to the invention may, for example, be so-called precipitation catalysts. Such catalysts can be prepared by precipitating their catalytically active components from their salt solutions, especially from the solutions of their nitrates and/or acetates, for example by adding solutions of alkali metal and/or alkaline earth metal hydroxide and/or carbonate solutions, for example sparingly soluble hydroxides, oxide hydrates, basic salts or carbonates, then drying the resulting precipitates and then converting them, by calcination at generally from about 300 to about 700° C., in particular from about 400 to about 600° C., to the corresponding oxides, mixed oxides and/or mixed-valency oxides, which are reduced by a treatment with hydrogen or with hydrogen-comprising gases at generally from about 50 to about 700° C, in particular from about 100 to about 400° C., to the metals and/or low-oxidation state oxidic compounds in question, and converted to the actual, catalytically active form. In general, reduction is effected until no further water is formed. In the preparation of precipitation catalysts which comprise a support material, the catalytically active components can be precipitated in the presence of the support material in question. The catalytically active components can advantageously also be precipitated from the salt solutions in question simultaneously with the support material.

In the process according to the invention, preference is given to using hydrogenation catalysts which comprise the metals or metal compounds which catalyze the hydrogenation deposited on a support material. Apart from the above-mentioned precipitation catalysts which, apart from the catalytically active components, additionally also comprise a support material, suitable support materials for the process according to the invention are generally those in which the catalytically hydrogenating components have been applied to a support material, for example by impregnation. The way in which the catalytically active metals have been applied to the support is generally not critical and may be accomplished in various ways. The catalytically active metals can be applied to these support materials, for example, by impregnation with solutions or suspensions of the salts or oxides of the elements in question, drying and subsequent reduction of the metal compounds to give the metals or lower-oxidation state compounds in question by means of a reducing agent, preferably with hydrogen or complex hydrides. Another means of applying the catalytically active metals to these supports consists in impregnating the supports with solutions of thermally readily decomposable salts, for example with nitrates or thermally readily decomposable complexes, for example carbonyl or hydrido complexes of the catalytically active metals, and heating the support thus impregnated to temperatures of from 300 to 600° C. for the purpose of thermal decomposition of the adsorbed metal compounds. This thermal decomposition is preferably undertaken under a protective gas atmosphere. Suitable protective gases are, for example, nitrogen, carbon dioxide, hydrogen or the noble gases. It is also possible for the catalytically active metals to be deposited on the catalyst support by vapor deposition or by flame spraying. The content of the catalytically active metals in these supported catalysts is in principle not critical for the success of the process according to the invention. It is self-evident to the person skilled in the art that higher contents of catalytically active metals in these supported catalysts can lead to higher space-time yields than lower contents. In general, supported catalysts whose content of catalytically active metals is from about 0.1 to about 90% by weight preferably from about 0.5 to about 40% by weight, based on the overall catalyst, are used. Since these content data are based on the overall catalyst including support material, but the different support materials have very different specific weights and specific surface areas, these values may also be below or above these data without this having an adverse effect on the result of the process according to the invention. It will be appreciated that it is also possible for a plurality of the catalytically active metals to be applied on the particular support material. It is also possible for the catalytically active metals to be applied to the support, for example, by the process of DE-A 2 519 817, EP-A 1477 219 and EP-A 285 420. In the catalysts according to the aforementioned documents, the catalytically active metals are present in the form of an alloy, which are obtained by thermal treatment and/or reduction, for example by impregnation with a salt or complex of the aforementioned metals.

Both the activation of the precipitated catalysts and of the supported catalysts can also be effected in situ at the start of the reaction by means of the hydrogen present but these catalysts are preferably activated separately before use.

The support materials used may generally be the oxides of aluminum and of titanium, zirconium dioxide, silicon dioxide, aluminas, for example montmorillonites, silicates such as magnesium or aluminum silicates, zeolites such as ZSM-5 or ZSM-10 zeolites, and activated carbon. Preferred support materials are aluminum oxides, titanium dioxides, silicon dioxide, zirconium dioxide and activated carbon. It will be appreciated that it is also possible for mixtures of different support materials to serve as the support for catalysts usable in the process according to the invention.

Examples of heterogeneous catalysts usable in the process according to the invention include the following: cobalt on activated carbon, cobalt on silicon dioxide, cobalt on aluminum oxide, rhenium on activated carbon, rhenium on silicon dioxide, rhenium/tin on activated carbon, rhenium/platinum on activated carbon, copper on activated carbon, copper/silicon dioxide, copper/aluminum oxide, copper chromite, barium copper chromite, copper/aluminum oxide/manganese oxide, copper/aluminum oxide/zinc oxide, and also the catalysts according to DE-A 3 932 332, U.S. Pat. No. 3,449,445, EP-A 44 444, EP-A 147 219, DE-A 3 904 083, DE-A 2 321101, EP-A 415 202, DE-A 2 366 264, EP 0 552 463 and EP-A 100 406.

To prepare substituted pyrrolidones starting from succinimide and diammonium succinate, the hydrogenation can be effected with the addition of the corresponding alcohols or amines.

In a further embodiment, in the process according to the invention, 2-pyrrolidone is alkylated in a gas phase or in a liquid phase. In a preferred embodiment 2-pyrrolidone is alkylated in the gas phase to give a branched or unbranched C1 to C20-N-alkylpyrrolidone or branched or unbranched N-hydroxyalkylpyrrolidone or branched or unbranched aminoalkylpyrrolidone; particular preference is given to the alkylation to N-methylpyrrolidone (NMP) and N-ethylpyrrolidone. In this case, pyrrolidone is reacted with alcohols, alkylamines, hydroxyalkylamines or dialkylamines at temperatures of from 100 to 400° C., preferably from 140 to 370° C., more preferably at from 180 to 350° C., and pressures (absolute) between 0.2 and 50 bar, preferably from 0.7 to 40 bar, more preferably from 0.8 to 20 bar. Alcohols are preferred. The alkylating agent is added preferably in excess, i.e., based on pyrrolidone, from 1.01 to 10 molar equivalents. Preference is given to from 1.1 to 3 molar equivalents. Catalysts which have acidic or basic sites are used. Typically, these are oxidic catalysts, for example aluminum oxide, silicon oxide, titanium oxide or else mixed oxides, for example aluminas, zeolites or the like.

In order to prepare substituted pyrrolidones, it is also possible in particular to add the alkylating agents mentioned below to the hydrogenation. To prepare an N-alkylpyrrolidone, particular preference is given to using a straight- or branched-chain C1 to C20-alcohol or -alkylamine, preferably a straight- or branched-chain C1 to C4-alcohol, for example methanol, ethanol, propanol or butanol, or a corresponding amine, for example methylamine, ethylamine, butylamine or propylamine. In one embodiment, alkylation is consequently effected in the presence of methanol or ethanol.

When the intention is, for example, to prepare NMP, it is possible to hydrogenate in the presence of methanol or methylamine. The higher the excess of alkylating agents, the higher the proportion of the corresponding product will be. When mixtures of pyrrolidone and the corresponding substituted pyrrolidone are not desired, pyrrolidone can be recycled into the reaction after the distillative workup.

In one embodiment, in the process according to the invention, succinimide is hydrogenated to 2-pyrrolidone.

In one embodiment, the reduction will be a gas or liquid phase hydrogenation which is performed under the following conditions:
   (i) at a temperature between about 80° C. and about 330° C., preferably between about 120° C. and about 300° C., more preferably between about 150° C. and about 280° C.;
   (ii) with a homogeneous or heterogeneous catalyst suitable for the hydrogenation of carbonyl groups, preferably of a catalyst which comprises one or more elements of groups 11, 6, 7, 8-10, 13, 14 or 15 of the Periodic Table of the Elements; preference is given to a catalyst based on copper, rhenium, manganese, cobalt, ruthenium, rhodium, nickel, palladium, iron, platinum, indium, tin or antimony, more preferably based on copper, cobalt, ruthenium or rhenium;
   (iii) at a pressure in the gas phase between about standard pressure and about 130 bar, preferably between about 2 and about 100 bar and more preferably between about 5 and about 60 bar, or at a pressure in the liquid phase between about 20 and about 400 bar, preferably between about 40 and about 300 bar, more preferably between about 120 and about 290 bar, and/or
   (iv) in the absence or in the presence of ammonia, preferably in the presence of an up to about 10-fold excess, more preferably in the presence of an up to about 5-fold excess, especially preferably in the presence of an up to about 2-old excess of ammonia, based on the reactant.

In one embodiment, the process is performed at the pressure mentioned and at the temperature mentioned and with the catalyst mentioned. The process is preferably performed under the conditions most preferred in each case.

Consequently, in one embodiment, the hydrogenation is performed in the gas phase at from about 150° C. to about 280° C. and at from about 5 to about 60 bar with catalysis of a catalyst based on copper, cobalt, ruthenium or rhenium and in the presence of an about 1-fold to about 2-fold excess of ammonia based on the reactant.

In a further embodiment of the present invention, the process according to the invention comprises the following step: alkylation of the compound IIIa with a branched or unbranched, saturated hydrocarbon having from 1 to about 20 carbon atoms and from 1 to 2 OH or $NH_2$ radicals, preferably 1 or 2 carbon atoms and 1 OH or $NH_2$ radical.

The alkylation can be effected in a liquid phase or in a gas phase.

For example, the alkylation can be performed in the gas phase under the following conditions:
   (i) at a temperature of from about 50 to about 600° C., preferably at from about 100 to about 500° C., more preferably from about 150 to about 450° C.;
   (ii) at a pressure of from about standard pressure to about 100 bar, preferably from about standard pressure to about 50 bar, more preferably from about standard pressure to 40 bar;
   (iii) using the alkylating component in a stoichiometric or superstoichiometric amount, preferably a superstoichiometric amount, more preferably in a ratio of from about 1 to about 10 mol/mol of pyrrolidone, more preferably from about 1 to about 5 mol/mol of pyrrolidone; and
   (iv) using a basic, neutral or Lewis- or Brønsted-acidic oxide or interoxide or mixed oxide, or a metal, preferably ruthenium, cobalt, nickel or copper, as a catalyst.

For example, the inventive alkylation can be performed in the liquid phase under the following conditions:
   (i) at a temperature of from about 50 to about 600° C., preferably at from about 100 to about 500° C., more preferably from about 150 to about 450° C.;
   (ii) at a pressure of from standard pressure to about 325 bar, preferably from about 10 to about 250 bar, more preferably from about 20 to about 200 bar;
   (iii) using the alkylating component in a stoichiometric or superstoichiometric amount, preferably a superstoichiometric amount, more preferably in a ratio of from about 1 to about 10 mol/mol of pyrrolidone, more preferably from about 1 to about 5 mol/mol of pyrrolidone; and
   (iv) using a basic, neutral or Lewis- or Brønsted-acidic oxide or interoxide or mixed oxide, or a metal, preferably ruthenium, cobalt, nickel or copper, as a catalyst.

Particular preference is given to performing the alkylation in the liquid phase.

In one embodiment, the process is performed at the pressure mentioned and at the temperature mentioned and with the catalyst mentioned. Preference is given to performing under the conditions most preferred in each case.

When the conversion in the alkylation is incomplete, the reactants can be recycled after distillative purification (for example batchwise or continuous distillation). In this case, low boilers, if present such as water, amine, ammonia, alcohol, are typically removed first in a first column and, if appropriate, recycled, if appropriate again after purification. The remaining product stream is then, if appropriate in a further column, separated further, in which case, if present, unconverted pyrrolidone of the formula III is removed and recycled.

In one embodiment, in the process according to the invention, a substituted or unsubstituted pyrrolidone is prepared. In one embodiment, the steps mentioned are combined in order to prepare an N-hydroxyalkylpyrrolidone or an N-alkylpyrrolidone, for example N-methylpyrrolidone (NMP). In one embodiment, a mixture of 2-pyrrolidone and N-methylpyrrolidone (NMP) is prepared.

Consequently, the present invention relates, in one embodiment, to a process which comprises the following steps:
fermentative preparation of a DAS solution with *E. coli*, *Anaerobiopirillum succiniproducens* or *Actinobacillus succinogenes* as the production strain from glucose, removal of the biomass, sterilization or pasteurization and concentration of the fermentation broth.

Ring closure of the DAS in the solution to give succinimide with simultaneous evaporation of $H_2O$ and $NH_3$ and purification of succinimide by distillation with virtually complete removal of the secondary components which disrupt the hydrogenation, the reaction and purification being performed in a continuous process under the following conditions: distillative removal of $H_2O$ and $NH_3$ at about standard pressure until, at approx. 150° C., a melt is present which is then, if appropriate, heated further up to about 250° C. for postreaction. Purification to remove secondary components by distillation at a temperature of about 190° C. and at a pressure of from about 20 to about 30 mbar. In the next step, the succinimide and succinic monoamide and/or diamide prepared is converted to 2-pyrrolidone by catalytic hydrogenation in the melt at about 250° C. and about 250 bar in the liquid phase with a homogeneous or heterogeneous catalyst suitable for the hydrogenation of carbonyl groups, preferably based on copper, cobalt, ruthenium or rhenium; in the presence of an up to about 2-fold excess of ammonia based on the reactant. In the next step, the 2-pyrrolidone prepared can be alkylated to N-methylpyrrolidone in the gas phase at a temperature of from about 150 to about 450° C.; at a pressure of from standard pressure up to about 6 bar, with methanol in a ratio of from more than 1 to about 5 mol/mol of pyrrolidone; with catalysis by an oxidic catalyst, for example comprising ruthenium, cobalt, nickel, copper or no metal addition.

TABLE 1

Simplified overview of a process: DAS → succinimide → 2-P → NMP, without specification, for example of a concentration, of a sterilization, inter alia. The ring closure with distillative purification has been shown in a block.

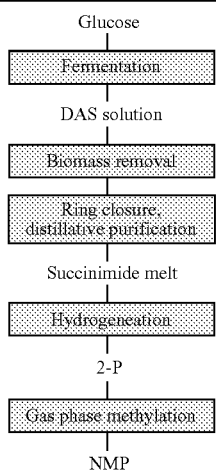

Glucose
↓
Fermentation
↓
DAS solution
↓
Biomass removal
↓
Ring closure, distillative purification
↓
Succinimide melt
↓
Hydrogeneation
↓
2-P
↓
Gas phase methylation
↓
NMP The examples which follow illustrate the invention and should not be interpreted in a restrictive manner.

EXAMPLES

Example 1

Fermentative Preparation of Succinic Acid

Media and Cultivation Conditions: Vemuri, Elteman and Altman, 2002, the Medium was Supplemented with Ampicillin and the pH Corrector NH4OH 1.1 Preparation of Master Cell Bank and Working Cell Bank A sample of the succinate production strain is streaked onto LB+glucose agar and incubated at 37° C. for 20 hours and then stored at +4° C. Selected colonies are then replicated further in LB+glucose liquid medium. LB+glucose liquid medium has the following composition: 10 g/l of tryptone, 5 g/l of yeast extract, 10 g/l of NaCl and 10 g/l of glucose. LB+glucose agar additionally contains 15 g/l of agar. Ready-prepared formulations can be purchased from Becton Dickinson GmbH, Heidelberg as Bacto LB Broth, Miller or Bacto LB-Agar, Miller. Addition of 10 g/l of glucose affords the media specified. Cultures of 20 ml, which have been obtained in 100 ml Erlenmeyer flasks, are incubated at 37° C. and 180 rpm on an agitated incubator (from Infors, Multitron type) for 15 hours. The cell suspension is subsequently centrifuged off with a laboratory centrifuge (from Heraeus, Biofuge Primo R; Rotor #7590, 50 ml Greiner PP centrifuge tubes, sterile) at 8500 rpm for 15 minutes. The cell pellet is resuspended in 10 ml of sterile LB+glucose liquid medium which has been supplemented with 20% glycerol. The resulting cell suspension is made up to 1 ml in aliquots under sterile conditions and stored at −70° C. These cultures are used as the master cell bank.

To prepare a working cell bank, sterile LB+glucose liquid medium is divided under sterile conditions into 20 ml portions in sterile 100 ml Erlenmeyer flasks. Subsequently, these flasks are inoculated under sterile conditions with 100 µl of the above-described master cell bank. The incubation is effected at 37° C. and 180 rpm for 15 hours on an agitated incubator (from Infors, Multitron type). Subsequently, the cell suspension is centrifuged off at 8500 rpm for 15 minutes with a laboratory centrifuge (from Heraeus, Biofuge Primo R; Rotor #7590, 50 ml Greiner PP centrifuge tubes, sterile). The cell pellet is resuspended in 10 ml of sterile LB+glucose liquid medium which has been supplemented with 20% glycerol. The resulting cell suspension is made up to 1 ml in aliquots under sterile conditions and stored at −70° C. These cultures are used as the working cell bank.

1.2 Preparation of a Succinate-Containing Fermentation Broth

A 1.0 ml aliquot of the working cell bank of the succinate production strain is removed from the freezer compartment and stored at room temperature for 10 minutes. 100 µl thereof are withdrawn under sterile conditions and distributed under sterile conditions with an inoculating loop on an LB+glucose agar plate. After incubation at 37° C. for 20 hours, the plate of cell material is withdrawn under sterile conditions and used to inoculate the preculture flasks (2000 ml round-bottom flasks with 4 chicanes, which comprise 300 ml of preculture medium). The preculture flasks are incubated at 37° C. and 110 rpm on an incubation shaker (from Infors, Multitron type) for six hours. For the start of the main culture, 3.5 l of batch medium are inoculated with 250 ml of the preculture. The cultivation is effected at 37° C. for 120 h in a stirred 5 l bioreactor (from Infors, ISF 100) with a 6-blade disk stirrer and four baffles, pH and $pO_2$ electrodes. Within the first 5.5 h (aerobic growth phase), the cultivation is effected at a constant speed of 900 rpm and sparging with sterile air (3.0 l/min), then switched to 250 rpm and sparging with sterile $CO_2$ gas (0.18 l/min). The pH is controlled to 7.0 at the start with 20% NaOH solution and 20% HCl soluftion. From 5.5 h, instead of NaOH solution, 25% NH4OH solution is used and the pH is regulated to 6.8. The feed medium is metered in according to a fixed metering profile which ensures that the glucose concentration in the fermentation broth is always between 10 and 30 g/l. For the feed metering, a balance (from Satorius, LP6200S), a metering module (from Satorius, YFC02Z-V2) and a pump (from Meredos, HP60) are used. During the cultivation, the course of the optical density is determined at a measurement wavelength of 600 nm ($OD_{600}$) with a photometer (from Pharmacia Biotech, Ultrospec 2000). The concentrations of glucose and succinate in the cell-free supernatant (filtration of the culture broth with Braun syringes, 2 ml injection and syringe filter attachment from Millipore, Millipore GP; Ø 33 mm; pore width 0.22 µm; PES Express membrane) are quantified by means of HPLC (stationary phase: Aminex HPX-87 H, 300×7.8 mm [from Biorad], mobile phase: 5 mM H2SO4, RI detection). At the end of the cultivation, the fermentation broth is discharged into 3 l Erlenmeyer flasks and sterilized at 121° C. in an autoclave for 20 minutes.

Before the further processing, the biomass is preferably removed, for example by means of laboratory centrifuge.

The preculture medium comprises the constituents specified in Table 2. To prepare the preculture medium, 22.0 g of glucose monohydrate, 10.0 g of yeast extract, 20.0 g of tryptone, 0.9 g of $K_2HPO_4 \cdot 3H_2O$, 1.14 g of $KH_2PO_4$, 0.25 g of $CaCl_2 \cdot 2H_2O$, 3.0 g of $(NH_4)_2SO_4$, 0.5 g of $MgSO_4 \cdot 7H_2O$, 20 ml of a biotin solution (50 mg/l, demineralized water as the solvent) and 1 ml of a thiamine solution (1 g/l, demineralized water as the solvent) were added to 0.95 liter of demineralized water. With stirring, the pH is adjusted to 7.0 with 2N NaOH solution, then the solution is made up to 1.0 liter with demineralized water. The sterilization is effected by sterile filtration through Stericups with Millipore Express PLUS membrane with pore width 0.22 μm (from Millipore).

TABLE 2

Preculture medium

| Medium constituent | Concentration |
| --- | --- |
| Glucose monohydrate | 22.0 g/l |
| Yeast extract | 10.0 g/l |
| Tryptone | 20.0 g/l |
| K$_2$HPO$_4$•3H$_2$O | 0.9 g/l |
| KH$_2$PO$_4$ | 1.14 g/l |
| CaCl$_2$•2H$_2$O | 0.25 g/l |
| (NH$_4$)$_2$SO$_4$ | 3.0 g/l |
| MgSO$_4$•7H$_2$O | 0.5 g/l |
| Biotin | 1.0 mg/l |
| Thiamine | 1.0 mg/l |

The batch medium for the main culture comprises the constituents specified in Table 3. To prepare the batch medium, 154.0 g of glucose monohydrate, 35.0 g of yeast extract, 70.0 g of tryptone, 3.15 g of K$_2$HPO$_4$.3H$_2$O, 3.99 g of KH$_2$PO$_4$, 088 g of CaCl$_2$. 2H$_2$), 10.5 g of (NH$_4$)$_2$SO$_4$, 1.75 g of MgSO$_4$.7H$_2$O, 70 ml of a biotin solution (50 mg/l, demineralized water as the solvent) and 3.5 ml of a thiamine solution (1 g/l, demineralized water as the solvent) are added to 3.30 liters of demineralized water. With stirring, the pH is adjusted to 7.0 with 2N NaOH solution, then the solution is made up to 3.5 liters with demineralized water, The sterilization is effected by sterile filtration by means of Stericups with Millipore Express PLUS membrane with pore width 0.22 μm (from Millipore).

TABLE 3

Batch medium for the main culture

| Medium constituent | Concentration |
| --- | --- |
| Glucose monohydrate | 44.0 g/l |
| Yeast extract | 10.0 g/l |
| Tryptone | 20.0 g/l |
| K$_2$HPO$_4$•3H$_2$O | 0.9 g/l |
| KH$_2$PO$_4$ | 1.14 g/l |
| CaCl$_2$•2H$_2$O | 0.25 g/l |
| (NH$_4$)$_2$SO$_4$ | 3.0 g/l |
| MgSO$_4$•7H$_2$O | 0.5 g/l |
| Biotin | 1.0 mg/l |
| Thiamine | 1.0 mg/l |

For the preparation of the feed medium, 550 g of glucose monohydrate are dissolved in 1 liter of demineralized water for the main culture. The sterilization is effected by sterile filtration through Stericups with Millipore Express PLUS membrane with pore width 0.22 μm (from Millipore).

Example 2

Reactive Distillation of DAS to Give Succinimide 2.1 1030 g of fermentation broth with approx. 13 g/l of diammonium succinate (=DAS) were supplemented with 58.5 g of approx. 95% synthetic diammonium succinate. The dry mass of the fermenter broth was approx. 7% there, the biomass is not removed.

The supplemented fermentation broth was concentrated on a rotary evaporator in a 2 l flask. After the concentration, a melt of approx. 150 ml remained, which was transferred into a 500 ml four-neck flask with PTFE stirrer, thermometer, hot plate and distillation system. At standard temperature, distillation was effected at 175° C. for 5 hours, then the temperature was raised to bottom temperature 250° C. and kept there for approx. 45 minutes. The pressure was then reduced to approx. 25 bar, and 26.7 g of product were distilled over at a distillation temperature of from 172 to 182° C.

The product comprised 88% succinimide. Succinic acid, monoamide or diamide were not detected.

2.2 Approx. 120 g of synthetic DAS with a purity of approx. 88% and 101 g of Pluriol P 600 were added to 1450 g of fermenter broth with approx. 30 g/l of DAS.

The fermenter broth was concentrated together with the Pluriol on a rotary evaporator. 317 g of distillation effluent were transferred into a heated dropping funnel on a 500 ml four-neck flask with hot plate, thermometer and solid distillation system. The four-neck flask was initially charged with 100 g of Pluriol P600. The Pluriol was preheated to from 240 to 250° C. The concentrated fermenter broth was added dropwise to the heated flask, and 23 g of product were simultaneously distilled off under reduced pressure (35 mbar) at a bottom temperature rising gradually to 310° C.

The product comprised 64% succinimide, approx. 4% monoamide and approx. 20% succinic acid or DAS.

2.3 684 g of 25% aqueous ammonia were initially charged in a 2000 ml two-neck flask with PTFE stirrer. Approx. 600 g of succinic acid were then added at max. 30° C. within 10 minutes (cooling with dry ice). The mixture was stirred for 1 hour until all of the succinic acid had dissolved. Thereafter, the pH was adjusted to pH 7 with aqueous ammonia. The minimal medium was added to the reaction solution and then the reaction mixture was concentrated on a rotary evaporator.

The residue was transferred to a 2000 ml four-neck flask with PTFE stirrer, thermometer, hot plate and distillation apparatus. The reaction mixture was heated gradually to a bottom temperature of 250° C. at standard pressure and initially water was distilled off. The mixture was stirred at 250° C. for a further hour. The bottoms were then cooled to 170° C. and vacuum was applied. At 26 mbar and a distillation temperature of from 179 to 185° C., 486 g of product were distilled off. The product comprised 92% succinimide. Diamide, monoamide and succinic acid were not detected as by-products.

In one variant of the experiment, the conversion of DAS to succinimide was performed in a thin-film evaporator. A 10% or 50% synthetic DAS solution was used and conducted through the thin-film evaporator in two stages. In the first stage, water and ammonia were distilled off under standard pressure. The partly converted melt ran into the bottom. Thereafter, the bottoms were heated at 250° C. to complete the reaction of DAS to give succinimide for approx. one hour. In the second step, the bottoms were conducted through the thin-film evaporator and the succinimide was distilled off via the top. The jacket temperature was 230° C. with a pressure of approx. 30 mbar. The addition of Pluriol E600 as a bottoms diluent has no influence on the result of the succinimide distillation in the second stage.

The jacket temperature for the thin-layer evaporator was 170° C. for a 50% DAS solution at a feed rate of 500 l/h, and 220° C. for a 10% solution at a feed rate of one liter per hour.

The reaction described was performed, as well as synthetic DAS, also for DAS in minimal medium and for a fermenter effluent supplemented with DAS. For better handling, the partly converted succinimide melts were each mixed with Pluriol E600. The results of the experiments are compiled in Table 4.

TABLE 4

Experimental results of the thin-film evaporator experiments

| Input | Succinimide content [% by weight] |
|---|---|
| Synth. DAS | 97 |
| Synth. DAS + Minimalm. + PI. | 85 |
| Synth. DAS + Fermenter + PI. | 87 |

Example 3

Hydrogenation

The catalyst used in all examples had been activated before use in a hydrogen stream and had the following composition before the hydrogen activation: 63.4% CoO, 18.1% CuO, 6.8% Mn3O4, 3.1% MoO3, 0.15% N2O, 3.3% H3PO4, the remainder up to 100% is water. The catalyst preparation is described, for example in DE-A 2 321101 or DE-A 3 904 083.

3.1 Preparation of Succinimide and its Hydrogenation 50 g/h of a 15% aqueous diammonium succinate solution were separated in a thin-film evaporator at 200° C. and standard pressure into a distillate fraction which comprises predominantly water (approx. 30 g/h) and a bottom product which comprised predominantly the succinate for 10 h. The bottom product was in turn reacted in a thin-film evaporator, this time at 250° C. and 50 mbar, as a melt with a feed temperature of approx. 120° C. (feed approx. 40 g/h). The distillate obtained (approx. 13 g/h) was predominantly succinimide with small contents of water and ammonia. As well as succinimide, the bottom product comprised the impurities from the original diammonium succinate solution. In total, approx. 65 g of succinimide were obtained, which were hydrogenated in an autoclave over 10 g of catalyst in the presence of 40 ml of 25% aqueous ammonia solution within 24 h. In the reaction effluent, pyrrolidone was found with 95% yield by means of quantitative gas chromatography analysis. In addition, approx. 2% succinimide, <0.1% gamma-butyrolactone, 1% pyrrolidine and a multitude of quantitatively insignificant products were present.

3.2 Conversion of Pyrrolidone to NMP

In an externally heatable reactor, over 55 g of acidic aluminum oxide, approx. 20 g/h of a 1:1 mixture of pyrrolidone and methanol (evaporation over a 20 ml glass ring bed upstream of the catalyst) were converted continuously at 300° C. In the reaction effluent, 48% unconverted pyrrolidone and 23.3% methanol, and also 27% NMP, were found.

3.3 Conversion of Pyrrolidone to NMP

Analogously to Example 3.2, instead of acidic aluminum oxide, 56 g of a catalyst consisting of 80% Al₂O₃/20% SiO2 were used. At 300° C., 48.1% pyrrolidone, 34.2% methanol and 16.2% NMP were found. After increasing the temperature to 350° C., 18% pyrrolidone, 17% methanol and 61.3% NMP were found in the effluent.

The invention claimed is:

1. A process for preparing a compound of formula (II) or a composition comprising said compound of formula (II)

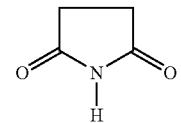

said process comprising the steps of:

(a) providing a fermentation broth comprising a compound a compound of formula (I)

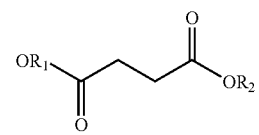

wherein $R_1$ is $NH_4^+$, H, or another cation; and $R_2$ is $NH_4^+$, H, or another cation;

with the proviso that at least one of $R_1$ or $R_2$ is $NH_4^+$;

(b) converting said compound of formula (I) in said fermentation broth to said compound of formula (II);

(c) simultaneously, intermittently, or subsequently distillatively removing ammonia and/or water from said fermentation broth;

(d) distilling the bottoms of the distillation of step (c) under reduced pressure to form a distillate comprising said compound of formula (II);

(e) isolating said compound of formula (II) or converting said distillate from step (d).

2. The process according to claim 1, wherein said compound II is obtained in a composition which further comprises a compound of formula (IIa)

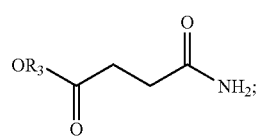

wherein $R_3$ is H or a cation; and/or a compound of formula (IIb)

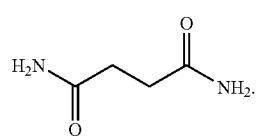

3. A process for preparing a compound of formula (IIIa) or a composition comprising said compound of formula (IIIa)

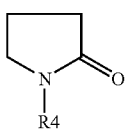

wherein R₄ is H;
said process comprising the steps of:
(a) providing a fermentation broth comprising a compound a compound of formula (I)

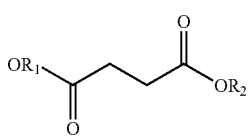

wherein
$R_1$ is $NH_4^+$, H, or another cation; and
$R_2$ is $NH_4^+$, H, or another cation;
with the proviso that at least one of $R_1$ or $R_2$ is $NH_4^+$;
(b) converting said compound of formula (I) in said fermentation broth to a compound of formula (II)

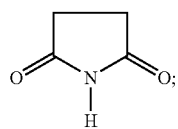

(c) simultaneously, intermittently, or subsequently distillatively removing ammonia and/or water from said fermentation broth;
(d) distilling the bottoms of the distillation of step (c) under reduced pressure to form a distillate comprising said compound of formula (II);
(e) isolating said compound of formula (II) or converting said distillate from step (d);
(f) reducing said compound of formula (II) to said compound of formula (IIIa).

4. A process for preparing a compound of formula (IIIb) or a composition comprising said compounds of formulas (IIIa) and (IIIb)

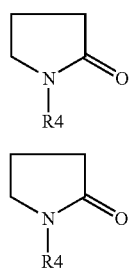

wherein
R₄ is H for compounds of formula (IIIa) and branched or unbranched alkyl having from up to 20 carbon atoms, optionally substituted with 0 to 2 OH or NH₂ radicals, for compounds of formula (IIIb);

said process comprising the steps of:
(a) providing a fermentation broth comprising a compound a compound of formula (I)

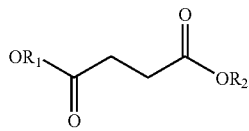

wherein
$R_1$ is $NH_4^+$, H, or another cation; and
$R_2$ is $NH_4^+$, H, or another cation;
with the proviso that at least one of $R_1$ or $R_2$ is $NH_4^+$;
(b) converting said compound of formula (I) in said fermentation broth to a compound of formula (II)

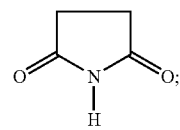

(c) simultaneously, intermittently, or subsequently distillatively removing ammonia and/or water from said fermentation broth;
(d) distilling the bottoms of the distillation of step (c) under reduced pressure to form a distillate comprising said compound of formula (II);
(e) isolating said compound of formula (II) or converting said distillate from step (d);
(f) reducing said compound of formula (II) to said compound of formula (IIIa);
(g) during or after step (f), completely or partially alkylating said compound of formula (IIIa) to give said compound of formula (IIIb).

5. The process according to claim 4, wherein pyrrolidone, hydroxyethylpyrrolidone and/or N-methylpyrrolidone (NMP) is prepared.

6. The process according to claim 1, wherein said converting and distillation steps are performed in a continuous process comprising the steps of:
(i) optionally removing the biomass and/or purifying said fermentation broth;
(ii) optionally concentrating said fermentation broth;
(iii) distillatively removing the by-products and converting said compound of formula (I) at a temperature of from 100° C. to 300° C.;
(iv) optionally postreacting at a temperature of from about 150° C. to about 300° C.; and
(v) distillatively removing said compound of formula (II) or said compound of formula (II) and said compounds of formulae (IIa) and/or (IIb) at a temperature of from 150° C. to 300° C. at standard pressure or at a pressure of from about 0.01 to about 1000 mbar.

7. The process according to claim 1, wherein said converting and distillation steps are performed in a batchwise process comprising the steps of:
(i) optionally removing the biomass and/or purifying said fermentation broth;
(ii) optionally concentrating said fermentation broth;
(iii) distillatively removing the by-products and converting said compound of formula (I) at a temperature of from room temperature to 300° C.;

(iv) optionally postreacting the distillate at a temperature of from about 150 °C. to about 300 °C. for less than 2 hours; and (v) optionally overdistillating the reaction mixture at a temperature of from 150 °C. to 300 °C. at standard or reduced pressure.

8. The process according to claim 1, wherein said fermentation broth, before the reaction of said compound of formula (I) or before distillation of said compound of formula (II) has up to 50% of a bottoms diluent added to it.

9. The process according to claim 4, wherein step (f) is achieved by hydrogenation.

10. The process according to claim 4, wherein step (f) is achieved by gas phase or liquid phase hydrogenation performed under the following conditions:

at a temperature between 80 °C. and 330 °C.;

(ii) in the presence of a homogeneous or heterogeneous catalyst suitable for the hydrogenation of carbonyl groups, said catalyst comprising one or more elements of group 11, 6, 7, 8-10, 13, 14, or 15 of the Periodic Table of the Elements; and/or (iii) in the gas phase at a pressure between standard pressure and 130 bar or in the liquid phase at a pressure between 20 and 400 bar.

11. The process according to claim 4, wherein step (g) is achieved by alkylating said compound of formula (IIIa) with a branched or unbranched, saturated hydrocarbon having from up to 20 carbon atoms, which are substituted with from 1 to 2 OH or $NH_2$ radicals.

12. The process according to claim 11, wherein step (g) is performed in the gas phase under the following conditions:

(i) at a temperature of from 50 °C. to 600 °C.;

(ii) at a pressure of from standard pressure to 100 bar;

(iii) in the presence of a basic, neutral, or Lewis- or Brønsted-acidic oxide or interoxide or mixed oxide or a metal; and wherein said hydrocarbon is used in a stoichiometric or superstoichiometric amount.

13. The process according to claim 11, wherein (g) is performed in the liquid phase under the following conditions:

(iv) at a temperature of from 50 °C. to 600 °C.;

(v) at a pressure of from standard pressure to 100 bar;

(vi) in the presence of a basic, neutral, or Lewis- or Brønsted-acidic oxide or interoxide or mixed oxide or a metal; and wherein said hydrocarbon is used in a stoichiometric or superstoichiometric amount.

* * * * *